United States Patent
Beckers et al.

(10) Patent No.: US 10,874,540 B2
(45) Date of Patent: Dec. 29, 2020

(54) PLASMA-ASSISTED ODOUR-FREE REGULATION OF GAS PRESSURE INSIDE STOMA BAG

(71) Applicant: Technische Universiteit Eindhoven, Eindhoven (NL)

(72) Inventors: Job Beckers, Son en Breugel (NL); Gerrit M. W. Kroesen, Eindhoven (NL)

(73) Assignee: Technische Universiteit Eindhoven, Eindhoven (NL)

( * ) Notice: Subject to any disclaimer, the term of this patent is extended or adjusted under 35 U.S.C. 154(b) by 259 days.

(21) Appl. No.: 16/091,213

(22) PCT Filed: Apr. 7, 2017

(86) PCT No.: PCT/EP2017/058354
§ 371 (c)(1),
(2) Date: Oct. 4, 2018

(87) PCT Pub. No.: WO2017/174767
PCT Pub. Date: Oct. 12, 2017

(65) Prior Publication Data
US 2019/0110919 A1    Apr. 18, 2019

Related U.S. Application Data

(60) Provisional application No. 62/319,713, filed on Apr. 7, 2016.

(51) Int. Cl.
*A61F 5/441* (2006.01)
*A61F 5/445* (2006.01)

(52) U.S. Cl.
CPC .............. *A61F 5/441* (2013.01); *A61F 5/445* (2013.01); *B01D 2257/90* (2013.01); *B01D 2259/818* (2013.01)

(58) Field of Classification Search
CPC ..... A61F 5/441; A61F 5/445; B01D 2257/90; B01D 2259/818
(Continued)

(56) References Cited

U.S. PATENT DOCUMENTS

| | | | | |
|---|---|---|---|---|
| 2,054,535 | A | * | 9/1936 | Diack ............... A61F 5/445 604/333 |
| 2004/0193122 | A1 | * | 9/2004 | Cline ............... A61F 5/448 604/332 |

(Continued)

OTHER PUBLICATIONS

Cursor, "Portable plasma to fight ostomy scents" Feb. 22, 2016. Retrieved from https://www.cursor.tue.nl/nieuwsartikel/artikel/draagbaar-plasma-tegen-nare-stomageurtjes/.
(Continued)

*Primary Examiner* — Andrew J Mensh
(74) *Attorney, Agent, or Firm* — Lumen Patent Firm (57) ABSTRACT

An ostomy pouching device is configured to allow two-way flow of gas between the device and a stoma bag (100). A check valve (104) is configured to allow ambient air into a channel of the device, and thereby into the stoma bag, when a pressure of the gas in the channel is less than a pressure of the ambient air; another check valve (105) is configured to allow gas to flow into a deodorizing reactor (110) when a pressure of the gas in the channel is greater than a pressure of the ambient air. The deodorizing reactor includes a plasma reactor configured to generate plasma in the channel for deodorizing the gas in the channel before being expelled from the device into the ambient air. The plasma reactor is preferably a dielectric barrier discharge (DBD) reactor. It may also include a secondary active carbon filter.

6 Claims, 6 Drawing Sheets

(58) Field of Classification Search
USPC .......................................................... 604/339
See application file for complete search history.

(56) References Cited

U.S. PATENT DOCUMENTS

2006/0251550 A1* 11/2006 Keras ................... H05H 1/2406
422/186.04
2009/0157140 A1* 6/2009 Martino ............. A61N 1/36007
607/41
2014/0360862 A1* 12/2014 Malik ..................... C01B 15/01
204/165

OTHER PUBLICATIONS

Eindhovens Dagblad, "New technology makes ostomy bags odor-free" Jan. 14, 2016. Retrieved from http://www.stomavereniging.com/Onze-vereniging/Informatievoorziening/Nieuwsberichten/Nieuwe-techniek-maakt-stomazakjes-geurvrij.

* cited by examiner

PLASMA-ASSISTED ODOUR-FREE REGULATION OF GAS PRESSURE INSIDE STOMA BAG

CROSS-REFERENCE TO RELATED APPLICATIONS

This application is a 371 of PCT application PCT/EP2017/058354 filed Apr. 7, 2017. PCT application PCT/EP2017/058354 claims the benefit of U.S. Provisional application 62/319,713 filed on Apr. 7, 2016.

FIELD OF THE INVENTION

The present invention relates generally to ostomy pouching systems and devices. More specifically, it relates to improved techniques for pressure regulation and deodorizing of gas discharged from ostomy pouching systems.

BACKGROUND OF THE INVENTION

Ostomy pouching systems (stoma bags) commonly have the problem of overpressure ('ballooning') and under-pressure ('pancaking'), resulting in unpredictable and unwanted leakage of intestine fluids and odorous gases. This problem has been addressed so far roughly by two means:

1) Chemical additions to the stoma bag. These chemicals might bond or react with the molecules responsible for the odours. A disadvantage of this approach is that it is not known exactly under what conditions, how much and for how long this would be a solution. Another disadvantage is irritation of stoma and skin.

2) Carbon filters which bond the gas emitted by the intestine and colon. A disadvantage of this approach is that these filters get saturated on too short time scales. Moreover, it is difficult to predict when this saturation will occur. Also, when these carbon filters get wet (they are installed in the bag's side walls) they clog.

BRIEF SUMMARY OF THE INVENTION

To overcome the problems with chemical additives (which only sometimes work) and carbon filters (which work well but are unpredictable in terms of lifetime), the present invention provides a new stoma bag design. Embodiments of the invention include a gas-regulation system that controls the process of equalizing the gas pressure inside a stoma bag with the outside ambient air while the exhausted gas is deodorized by a miniaturized plasma device.

In one aspect, the invention provides an ostomy pouching device. The device includes a port for connecting the device to a stoma bag, configured to allow gas to flow between the device and the stoma bag; a channel through which gas may flow; a restrictor valve in the channel regulating a rate of gas flow; a pressure transducer connected to the channel for measuring a pressure of the gas in the channel; a first check valve connected to the channel, configured to allow ambient air into the channel when a pressure of the gas in the channel is less than a pressure of the ambient air; a deodorizing reactor comprising a plasma reactor configured to generate plasma in the channel for deodorizing the gas in the channel; a second check valve connected to the channel, configured to allow gas to flow into a deodorizing reactor when a pressure of the gas in the channel is greater than a pressure of the ambient air; an variable voltage (e.g., pulsed) power supply connected to the deodorizing reactor, configured to generate high voltage pulses that drive the plasma reactor; a battery providing electrical power to the pulsed power supply; and a microcontroller circuit configured to control the second check valve to allow gas to flow into the deodorizing reactor when the pressure transducer measures an ambient pressure lower than a pressure of the gas in the channel, and to control the pulsed power supply to activate the deodorizing reactor when the second check valve allows gas to flow into the deodorizing reactor.

Preferably, the deodorizing reactor comprises a dielectric barrier discharge (DBD) reactor. It may also include an active carbon filter. The dielectric barrier discharge (DBD) reactor may include a high voltage electrode positioned within a channel of the plasma chamber, a grounded electrode, and a dielectric material between the high voltage electrode and the grounded electrode. In some embodiments, the wires HV and ground can be switched.

DETAILED DESCRIPTION OF THE INVENTION

The problem of ballooning and pancaking of stoma bags is solved by regulating the gas pressure inside a stoma bag. Released gas is deodorized using a miniature plasma device.

Figure 1:
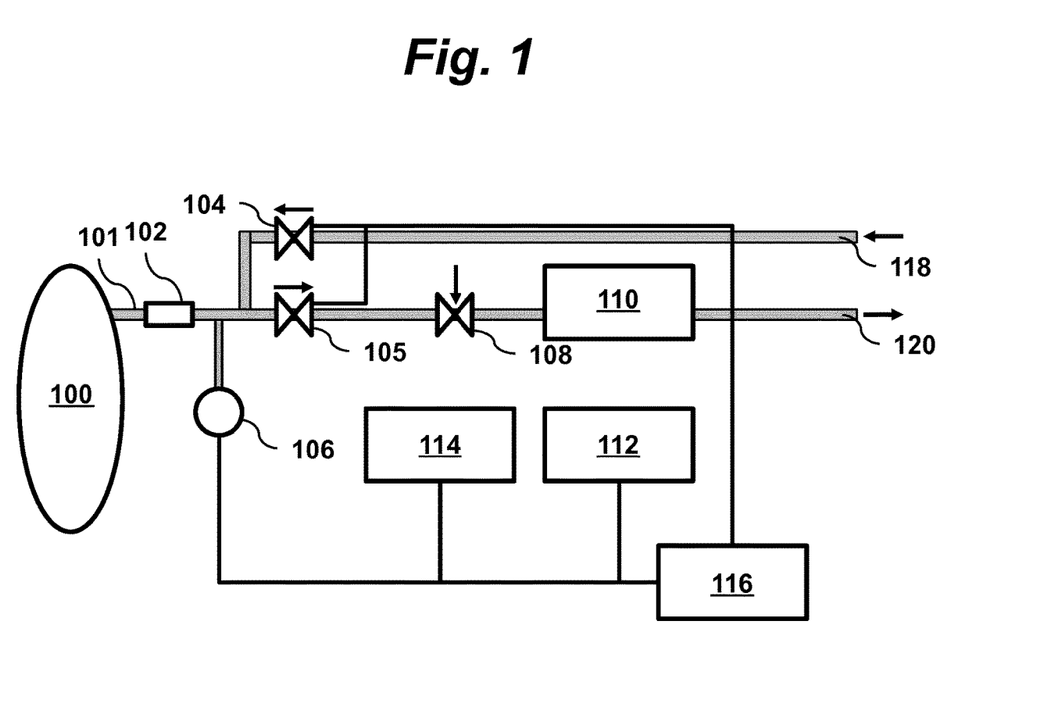
FIG. 1 is a schematic illustration of an ostomy pouching device, according to an embodiment of the invention.

Schematically, an embodiment of the invention is shown in FIG. 1. The device includes a membrane filter 102 (preventing liquid to enter the device from stoma bag 100), a thin flexible tube 101 connecting the stoma bag to the membrane filter, a pressure sensor 106 (detecting over- or under-pressure inside the stoma-bag), two check valves 104, 105 (either passively or actively operating), a needle valve or natural gas obstruction 108 (ensuring constant gas flow), and a plasma device 110 for deodorization of the exhausted gas. The device also includes a battery pack 114, miniaturized pulsed power supply 112, and a microcontroller circuit 116. An input port 118 receives air from outside, while an output port 120 expels air from inside the device.

During operation, there is continuous regulation of the total gas pressure inside the stoma bag. When the pressure inside the stoma bag is lower than ambient pressure, check valve 104 (only allowing gas flow towards the stoma bag) is opened (either passively or actively) and allows ambient air to flow in through input port 118 and equilibrate the pressure in the stoma bag.

When the pressure inside the stoma bag is higher than ambient pressure, a different check valve 105 (only allowing gas flow from the stoma bag outwards) is opened (either passively or actively), after which the gas flow is regulated by a needle valve 108 (or a natural obstruction limiting the gas flow), and guided through a gas cracker 110 such as a plasma chamber where the odorous molecules in the intestine gas from the stoma bag will be cracked by the highly energetic plasma species. The latter occurs at room temperature. After being treated by the plasma, the gas is exhausted through output port 120 into the ambient air. In the gas cracker 110, the generated plasma is either based on a series of pulsed corona discharges with applied voltages in the range 1-10 kV and pulse rise-times of about 1-10 nanoseconds, or based on a dielectric barrier discharge (DBD) in flat or cylindrical geometry.

The whole system is controlled by a microcontroller circuit 116 and operates on rechargeable batteries 114 for at least 24 hours. The micro-controller circuit 116 reads out the signals from pressure sensor 106 and based on that information controls gas valves 104, 105 and plasma power supply 112. Specifically, power is provided from the plasma power supply 112 to the plasma chamber 110 only when the pressure in the stoma bag is higher than ambient pressure and gas is being discharged.

Furthermore, the whole system—as being the collection of gas regulating system, micro-control system, plasma device, electrical plasma source and battery pack—is miniaturized such that it preferably does not exceed the dimensions of $150 \times 100 \times 50$ mm$^3$. Due to this small volume, the system is a wearable device which is connected to the stoma bag by a thin flexible tubing 101 and therefore can be worn anywhere on or near the body.

Advantageously, the device controls the gas pressure inside the stoma bag while the exhausted gas is deodorized using plasma. In contrast, existing techniques for gas and odour cleaning using plasma are limited to applications to decompose gas at high flow rates and on industrial scales (mainly petrochemical industries). On the other hand, no existing techniques for odour reduction in ostomy pouching systems contemplate the use of gas cracking with plasma.

Figure 2A:
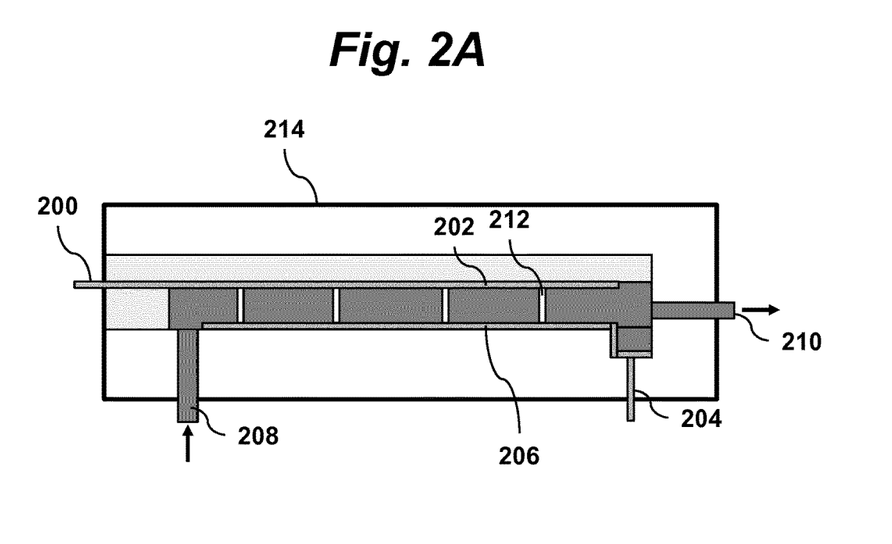
FIG. 2A is a top view of a plasma chamber according to an embodiment of the invention.
Figure 2B:
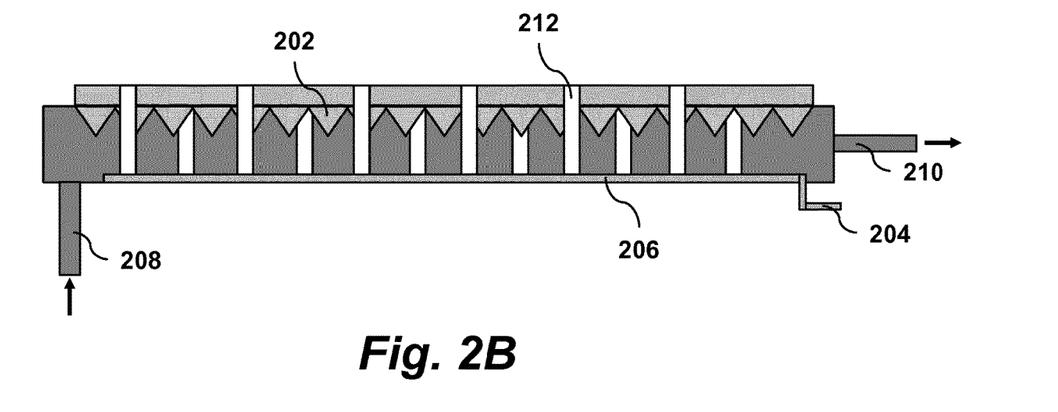
FIG. 2B is a side view of a plasma chamber according to an embodiment of the invention.

FIG. 2A shows a top view and FIG. 2B shows a side view of a plasma chamber according to an embodiment of the invention. In this embodiment, the plasma is generated by a series of pulsed corona discharges. In this pulsed corona discharge embodiment, the chamber includes a high voltage electrode connector 200, a high voltage electrode array 202. For miniaturization-purposes of the plasma chamber, the multiple high voltage electrodes can for instance be made out of one plate in the form of a series of saw tooths. A grounded/floating electrode 206 attached to connector 204 is positioned opposite the electrode array 202. This counter electrode may be a slab of aluminium or stainless steel attached against one of the plasma chamber walls. Gas enters the chamber through input 208, flows through the gap between electrodes 202 and 206, then exits through output 210. Since the gas channel is relatively long and corona discharge does not fully fill the whole cross sectional area, structures 212 may be used to partially obstruct the gas flow moving through the channel. These structures may be made from the side walls, forcing the gas to mix sufficiently. In operation, high voltage is applied for a duration of time in order to guarantee sufficient residence time of the gas molecules in the plasma volume. A housing 214 made of an insulating material encloses and secures the components of the chamber.

Figure 3A:
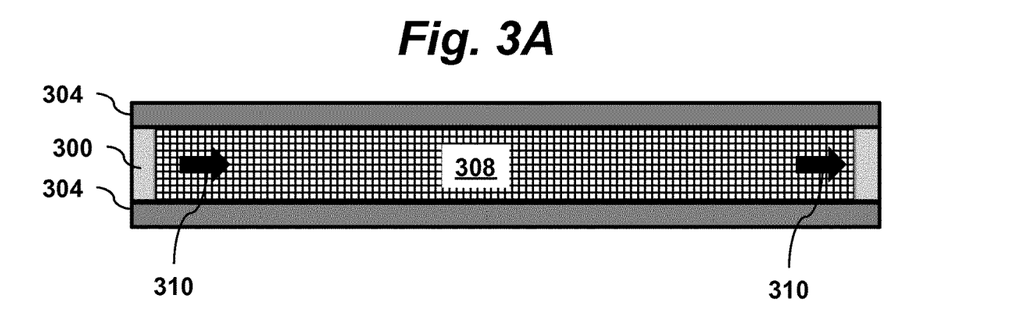
FIGS. 3A-C show views of a dielectric barrier discharge (DBD) reaction chamber design using a flat geometry, according to an embodiment of the invention.
Figure 3B:
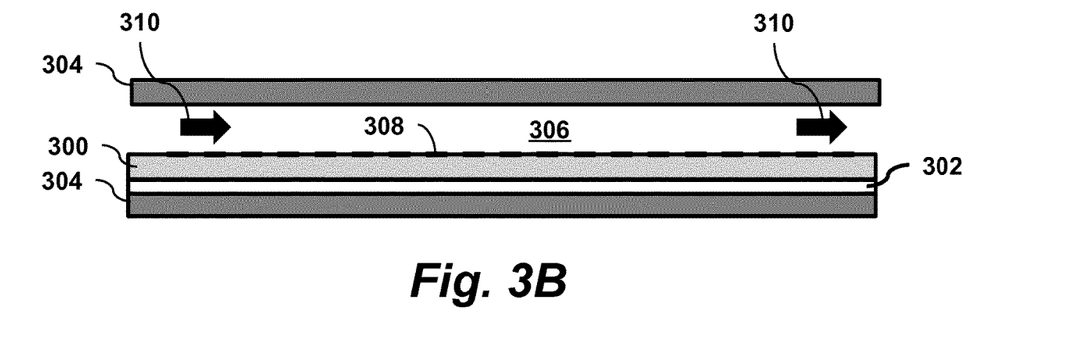
Figure 3C:
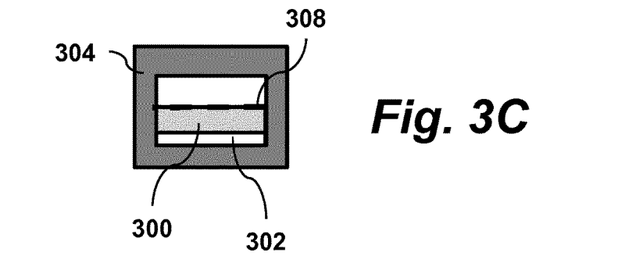
Figure 4A:
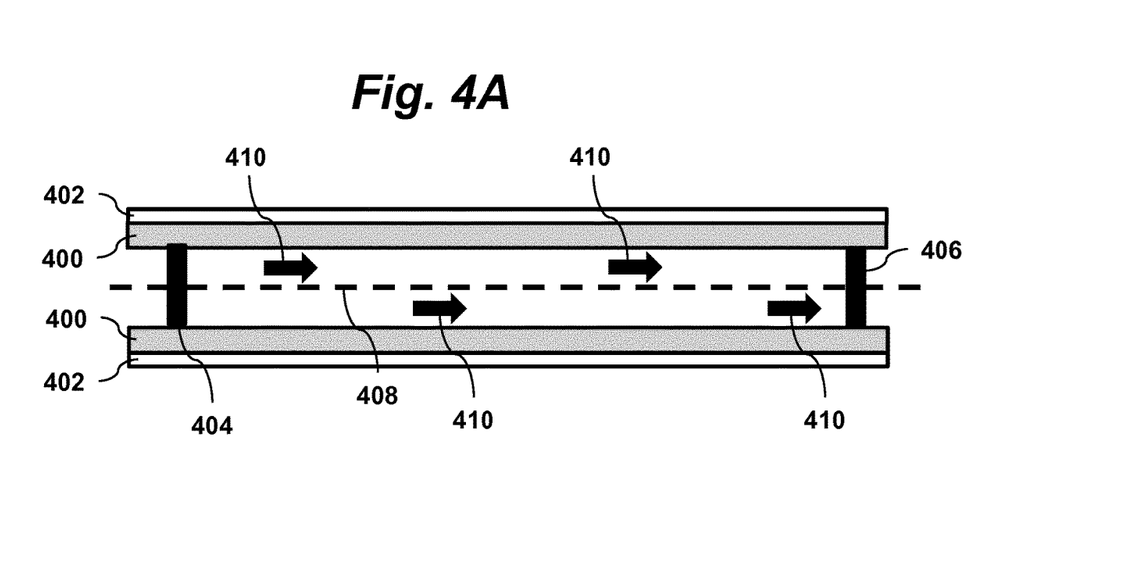
FIGS. 4A-B show views of a dielectric barrier discharge (DBD) reaction chamber design using a cylindrical geometry, according to an embodiment of the invention.
Figure 4B:
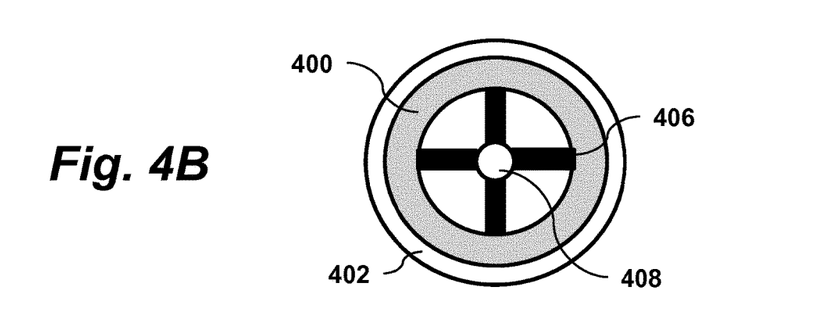

In an alternative embodiment, the plasma may be generated by a dielectric barrier discharge (DBD). This embodiment may be implemented with various geometries, such as a flat geometry (FIGS. 3A-C) or a cylindrical geometry (FIGS. 4A-B). In both designs there is a dielectric chamber housing (e.g., glass) with a grounded or floating electrode on the exterior and a high voltage electrode on the inside in the channel where the intestine gas flows.

The flat geometry implementation (FIGS. 3A-C) includes a hollow squared bar 304 forming the chamber's wall that encloses a channel 306. The wall may be made of a material such as plastic, PEEK, Nylon, Plastic, Teflon, or any other insulator that is chemically and physically resistive against plasma-produced species. Inside the channel, a piece of thin glass 300 (in the order of mm thickness) is covers a grounded or floating electrode 302, which is made of stainless steel, aluminium, copper or any other conductor. A fine mesh 308 made of stainless steel, aluminium, copper or any other conductor functions as a high voltage electrode. The mesh 308 is positioned parallel to the electrode 302, both of which extend along the length of the chamber. When the high voltage signal is switched on, plasma will be generated above the mesh grid and will interact with the intestine gas 310 flowing through the channel 306.

In an alternate embodiment, instead using meshes mounted to the dielectric surface for the high voltage electrode, a stainless steel wool material is used. This has the advantage of igniting and sustaining the plasma on lower voltages since there are per definition numerous sharp edges inducing significant field-enhancement.

The cylindrical geometry (FIGS. 4A-B) is made of a glass (or flexible tubing material) cylinder 400 with a grounded or floating electrode 402 on the outside. Electrode 402 may be made of thin sticky aluminium tape or a deposited conducting coating. Along the axis, inside the cylinder, is a high voltage electrode 408, which may be made of stainless steel, aluminium or copper wire or wires of any other conductor that is chemically and physically resistive against plasma-produced species. Note that high voltage and ground on the different electrodes (inside/outside) can be reversed in some embodiments. At the ends of the chamber and also along additional positions along the chamber axis are radially positioned beams 404, 406 that support the central electrode 408. When the high voltage signal is switched on to the central electrode, plasma will be generated inside the glass tube where the intestine gas 410 flows. Note that the path length of the gas through the plasma region—and therefore also the residence time—can be increased, for example, using flexible tubing that may be folded or winded.

The variable voltage power supply 112 (FIG. 1) generates a sine wave or pulsed voltage. It may be implemented in various ways. For the geometry with pulsed corona discharges (FIGS. 2A-B), gap distances of only a few mm and ultrashort (~100 ns) pulses with extremely high voltage rise times (~ns/kV) are used. The driving power supply delivers several kV with rise times of only a few nanoseconds, pulse lengths of approximately a few 100 ns and repetition rates flexible but in the order of 10-100 kHz. For the geometry with the DBD (FIGS. 3A-C and FIGS. 4A-B) slower voltage signals, which are pulsed/AC can be used. Parameters used here are frequency 10-100 kHz, more specifically (20-30 kHz) at voltages of 1-10 kV. In any case, either of the power supplies are switched on/off by a 0-5 V signals from the control system 116.

The control system 116 receives from pressure transducer 106 measurements of the pressure in the stoma bag 100, controls opening and closing of the check valves 104, 105 (in embodiments where the valves are actively controlled) and controls the power supply 112 of the plasma chamber 110. For example, in a specific implementation, the microcontroller circuit 116 is based on Arduino boards (e.g. the Arduino NANO with small form factor). Check valves 104, 105 are controlled with 5 V (supplied directly by Arduino) or 12 V (supplied by battery pack, through relays controlled by Arduino) signals. A 0-5 V directly supplied by Arduino will control the power supply (only if gas is exhausted) in terms of on/off.

The battery pack 114 delivers 3.7 V. An electronic system (not shown) in the pack is used to transform up to 12 V DC, which is fed into relays that are controlled by the microcontroller to provide power to the check valves 104, 105 and the pulsed power supply 112.

Figure 5A:
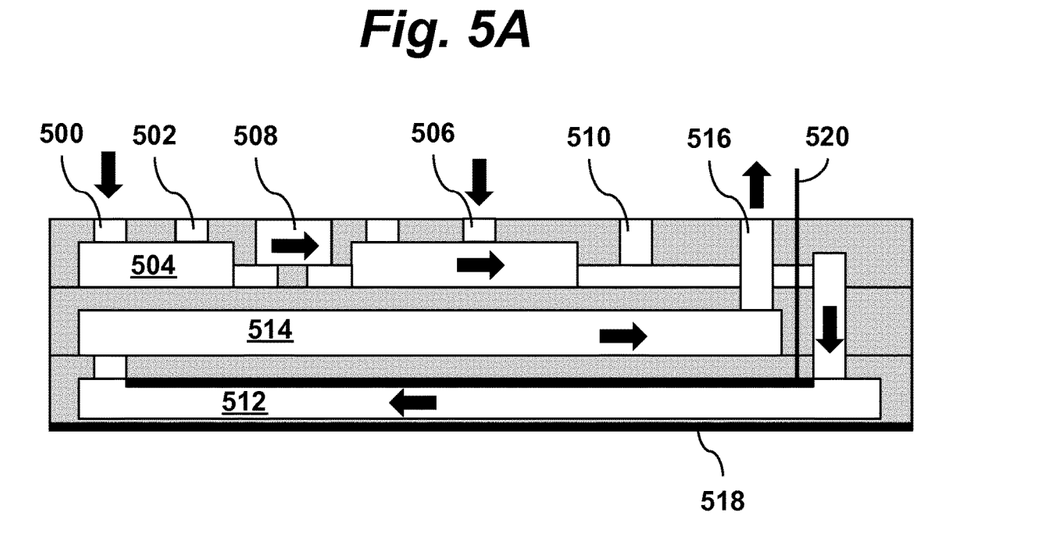
FIGS. 5A-B show views of a specific realization of a gas flow component of a device according to an embodiment of the invention.
Figure 5B:
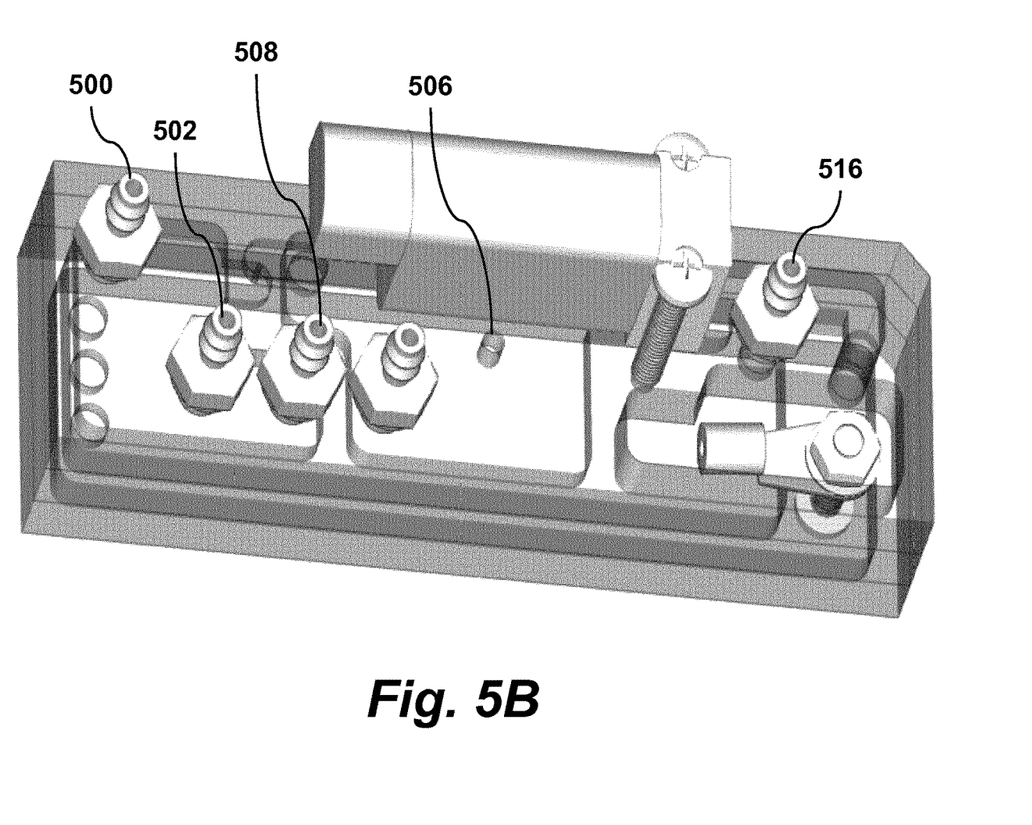

FIGS. 5A-B show side and perspective views of a specific realization of a gas flow component of a device according to an embodiment of the invention. The device has an input port 500 for connecting the device to a stoma bag via flexible tubing. The incoming gas flows through a passage 504 and past a port 502 for connecting a pressure transducer that measures the gas pressure inside the stoma bag. A flow restrictor 508 ensures even flow, preventing sudden bursts of gas from passing through the device. Flow resistor 508 may be used to measure the pressure difference. If the sensed pressure by transducer 502 is lower than ambient pressure, valve 506 is opened (both options active and passive valves are possible), allowing ambient air to flow into the device, equalizing the pressure inside the stoma bag with ambient pressure. If the sensed pressure is higher than ambient pressure, valve 510 will be opened (actively). Opening valve 510 allows gas from the stoma bag to pass through a deodorizing region that includes plasma reactor 512 and passive reactor 514. The deodorized gas is then released through output port 516 to the environment. The plasma reactor 512 preferably houses a dielectric barrier discharge 'cracking' odorous molecules from the gas, as described in relation to FIGS. 3A-C or FIGS. 4A-B. The dielectric barrier discharge (DBD) reactor 512 has high voltage connection 520 and ground connection 518. It is powered by 10-30 kHz, 2-10 kV voltage signal. The passive reactor 514 may be an empty channel that serves to enhance the reaction time of plasma species. Alternatively, passive reactor 514 may be filled with activated carbon to clean the gas from possible access of ozone. The components in FIG. 5 are contained in a housing which may have dimensions, for example, 80 mm×20 mm×20 mm.

Figure 6:
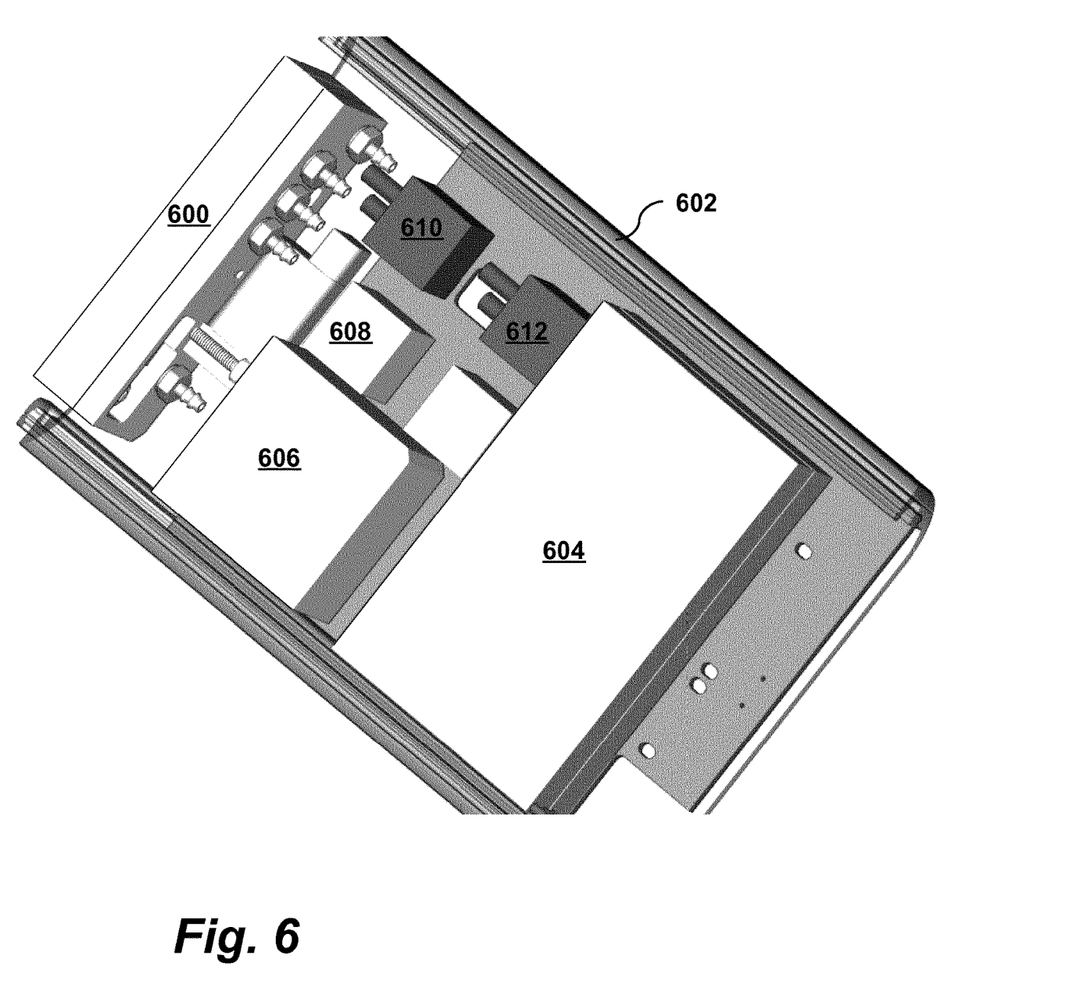
FIG. 6 is a perspective view of a device according to an embodiment of the present invention.

FIG. 6 is a perspective view of a device according to an embodiment of the present invention. Gas flow component 600, as described in relation to FIGS. 5A-B is mounted in a housing 602 together with battery pack 604, pulsed power supply 606, electronic controller 608, and pressure transducers 610, 612. Plastic gas tubes and electrical wires (not shown) connect the components.

The invention claimed is:

1. An ostomy pouching device comprising:
    a port for connecting the device to a stoma bag, configured to allow gas to flow between the device and the stoma bag;
    a channel through which gas may flow;
    a restrictor valve in the channel regulating a rate of gas flow;
    a pressure transducer connected to the channel for measuring a pressure of the gas in the channel;
    a first check valve connected to the channel, configured to allow ambient air into the channel when a pressure of the gas in the channel is less than a pressure of the ambient air;
    a deodorizing reactor comprising a plasma reactor configured to generate plasma in the channel for deodorizing the gas in the channel;
    a second check valve connected to the channel, configured to allow gas to flow into a deodorizing reactor when a pressure of the gas in the channel is greater than a pressure of the ambient air;
    an variable voltage power supply connected to the deodorizing reactor, configured to generate high voltage pulses that drive the plasma reactor;
    a battery providing electrical power to the pulsed power supply;
    a microcontroller circuit configured to control the second check valve to allow gas to flow into the deodorizing reactor when the pressure transducer measures an ambient pressure lower than a pressure of the gas in the channel, and to control the pulsed power supply to activate the deodorizing reactor when the second check valve allows gas to flow into the deodorizing reactor.

2. The ostomy pouching device of claim 1, wherein the deodorizing reactor comprises a dielectric barrier discharge (DBD) reactor.

3. The ostomy pouching device of claim 2, wherein the deodorizing reactor further comprises an active carbon filter.

4. The ostomy pouching device of claim 2, wherein the dielectric barrier discharge (DSD) reactor comprises a high voltage electrode positioned within a channel of the plasma chamber, a grounded electrode, and a dielectric material between the high voltage electrode and the grounded electrode.

5. The ostomy pouching device of claim 2, wherein the dielectric barrier discharge (DBD) reactor comprises a grounded electrode positioned within a channel of the plasma chamber, a high voltage electrode, and a dielectric material between the high voltage electrode and the grounded electrode.

6. The ostomy pouching device of claim 2, wherein the dielectric barrier discharge (DBD) reactor comprises a grounded electrode, a high voltage electrode comprising steel wool, and a dielectric material between the high voltage electrode and the grounded electrode.

* * * * *